(12) United States Patent
Manivannan et al.

(10) Patent No.: US 7,854,349 B2
(45) Date of Patent: *Dec. 21, 2010

(54) SHAVE GEL PRODUCTS

(75) Inventors: Gurusamy Manivannan, Maryland Heights, MO (US); Alexander Novikov, Framingham, MA (US); Stephen Thong, Needham, MA (US); Alfred Barnet, Hingham, MA (US); Yun Xu, Andover, MA (US); Ronald McLaughlin, Medford, MA (US)

(73) Assignee: The Gillette Company, Boston, MA (US)

( * ) Notice: Subject to any disclaimer, the term of this patent is extended or adjusted under 35 U.S.C. 154(b) by 1587 days.

This patent is subject to a terminal disclaimer.

(21) Appl. No.: 10/720,531

(22) Filed: Nov. 25, 2003

(65) Prior Publication Data

US 2004/0166086 A1    Aug. 26, 2004

Related U.S. Application Data

(63) Continuation-in-part of application No. 10/371,619, filed on Feb. 21, 2003, now abandoned.

(51) Int. Cl.
*B65D 35/22* (2006.01)
*A61K 8/19* (2006.01)

(52) U.S. Cl. .......................... 222/94; 424/73
(58) Field of Classification Search .............. 424/70, 424/73; 222/94; 252/183.14
See application file for complete search history.

(56) References Cited

U.S. PATENT DOCUMENTS

| | | | |
|---|---|---|---|
| 1,042,569 A | 10/1912 | Lang | |
| 2,995,521 A | 8/1961 | Bluard | |
| 3,241,722 A | 3/1966 | Nissen | |
| 3,341,418 A | 9/1967 | Moses et al. | |
| 3,454,198 A | 7/1969 | Flynn | |
| 3,484,378 A | 12/1969 | Reich et al. | |
| 3,488,287 A | 1/1970 | Seglin et al. | |
| 3,499,844 A | 3/1970 | Kibbel, Jr. et al. | |
| 3,541,581 A | 11/1970 | Monson | |
| 3,574,118 A | 4/1971 | Baker | |
| 3,585,982 A | 6/1971 | Hollinshead | |
| 3,638,786 A | 2/1972 | Borecki et al. | |
| 3,639,574 A | 2/1972 | Schmolka | |
| 3,651,931 A | 3/1972 | Hsiung | |
| 3,722,752 A | 3/1973 | Kenkare et al. | |
| 3,723,324 A | 3/1973 | Pierce et al. | |
| 3,772,203 A | 11/1973 | Gray | |
| 3,819,524 A | 6/1974 | Schubert et al. | |
| 3,865,930 A | 2/1975 | Abegg et al. | |
| 3,866,800 A * | 2/1975 | Schmitt | 222/94 |
| 3,878,118 A | 4/1975 | Watson | |
| 3,891,827 A | 6/1975 | Wyse | |
| 3,931,912 A | 1/1976 | Hsiung | |
| 3,966,090 A | 6/1976 | Prussin et al. | |
| 3,997,083 A | 12/1976 | McNair | |
| 4,010,872 A | 3/1977 | Lozano et al. | |
| 4,042,520 A | 8/1977 | Frump et al. | |
| 4,056,707 A | 11/1977 | Farnam | |
| 4,069,949 A | 1/1978 | Ryckman, Jr. | |
| 4,088,751 A | 5/1978 | Kenkare et al. | |
| 4,110,426 A | 8/1978 | Barnhurst et al. | |
| 4,130,501 A | 12/1978 | Lutz et al. | |
| 4,343,785 A | 8/1982 | Schmolka | |
| 4,387,833 A | 6/1983 | Venus, Jr. | |
| 4,405,489 A | 9/1983 | Sisbarro | |
| 4,439,416 A | 3/1984 | Cordon et al. | |
| 4,465,663 A | 8/1984 | Schmolka | |
| 4,528,111 A | 7/1985 | Su | |
| 4,651,503 A | 3/1987 | Anderson, III et al. | |
| 4,687,663 A | 8/1987 | Schaeffer | |
| 4,788,052 A | 11/1988 | Ng et al. | |
| 4,839,081 A | 6/1989 | Church et al. | |
| 4,839,156 A | 6/1989 | Ng et al. | |
| 4,849,213 A | 7/1989 | Schaeffer | |
| 4,892,729 A | 1/1990 | Cavazza | |
| 4,895,721 A | 1/1990 | Drucker | |
| 4,964,540 A | 10/1990 | Katz | |
| 5,059,417 A | 10/1991 | Williams et al. | |
| 5,248,495 A | 9/1993 | Patterson et al. | |
| 5,308,643 A | 5/1994 | Osipow et al. | |
| 5,326,556 A | 7/1994 | Barnet et al. | |

(Continued)

FOREIGN PATENT DOCUMENTS

CN    CA 48-35154    10/1973

(Continued)

OTHER PUBLICATIONS

Herbert Boden, "Hot Shave Lather Technology," "Freon" Products Laboratory, E.I. du Pont Nemours & Company (1968).

(Continued)

*Primary Examiner*—Kevin Weddington
(74) *Attorney, Agent, or Firm*—Ronald T. Sia; Kevin C. Johnson; Steven W. Miller

(57) ABSTRACT

Self-heating, post-foaming shave gels and shave gel products are provided. In some implementations, the shave gels include a non-ionic emulsifier system, e.g., including one or more fatty alcohol ethoxylates.

20 Claims, No Drawings

U.S. PATENT DOCUMENTS

| | | | |
|---|---|---|---|
| 5,538,720 | A | 7/1996 | Jendryssek-Pfaff et al. |
| 5,550,211 | A | 8/1996 | DeCrosta et al. |
| 5,560,859 | A | 10/1996 | Hartmann et al. |
| 5,858,343 | A | 1/1999 | Szymczak |
| 6,056,946 | A | 5/2000 | Crudele et al. |
| 6,250,505 | B1 | 6/2001 | Petit |
| 6,682,726 | B2 * | 1/2004 | Marchesi et al. .............. 424/73 |
| 2002/0017532 | A1 | 2/2002 | Aiken et al. |
| 2002/0020407 | A1 | 2/2002 | Wohland et al. |

FOREIGN PATENT DOCUMENTS

| | | |
|---|---|---|
| DE | 31 39 465 A1 | 4/1983 |
| EP | 0339634 A1 * | 11/1989 |
| EP | 0 734 781 A1 | 3/1996 |
| EP | 1 175 895 A2 | 1/2002 |
| FR | 1468909 | 11/1965 |
| FR | 2060247 | 9/1969 |
| JP | 2001323258 A | 11/2001 |
| NL | 6602701 | 9/1966 |
| WO | WO 02/47636 A2 | 6/2002 |

OTHER PUBLICATIONS

Solvay Interox, "Solvay Interox Formulary Guide Gelled Hydrogen Peroxide," Peroxygens, Techniccal Data Sheet (Apr. 1994).

Decision on Appeal by the BPAI, U.S. Appl. No. 10/199,407, filed Jul. 19, 2002, Alexander Novikov, 7 pages.

* cited by examiner

SHAVE GEL PRODUCTS

CROSS-REFERENCE TO RELATED APPLICATIONS

This application is a continuation-in-part application of and claims priority to U.S. application Ser. No. 10/371,619, filed on Feb. 21, 2003, now abandoned hereby incorporated by reference in its entirety.

TECHNICAL FIELD

This invention relates to self-heating post-foaming shave gel products

BACKGROUND

Currently, a widely used form of shaving preparation is the type referred to as a post-foaming shave gel. These post-foaming shave gels are now well-known and have been described, for example, in U.S. Pat. No. 2,995,521 (Bluard), U.S. Pat. No. 3,541,581 (Monson), U.S. Pat. No. 4,405,489 (Sisbarro), U.S. Pat. No. 4,528,111 (Su), U.S. Pat. No. 4,651,503 (Anderson), U.S. Pat. No. 5,248,495 (Patterson), U.S. Pat. No. 5,308,643 (Osipow), U.S. Pat. No. 5,326,556 (Barnet), U.S. Pat. No. 5,500,211 (George), U.S. Pat. No. 5,560,859 (Hartmann), U.S. Pat. No. 5,858,343 (Szymczak) and WO 02/47636 (Lasota). Such compositions generally take the form of an oil-in-water emulsion in which the post-foaming agent, generally a volatile (i.e., low boiling point) aliphatic hydrocarbon, is solubilized in the oil phase, and the water phase comprises a water-dispersible soap or interrupted soap component. The product is generally packaged in an aerosol container with a barrier, such as a piston or collapsible bag, to separate the post-foaming gel from the propellant required for expulsion of the product. The product is dispensed as a clear, translucent or opaque gel that is substantially free from foaming until it is spread over the skin, at which time it produces a foam lather generated by the volatilization of the volatile hydrocarbon foaming agent.

Users of wet-shave razors generally appreciate a feeling of warmth against their skin during shaving. The warmth feels good, and also causes the user's skin to hydrate and beard to soften, resulting in a more comfortable shave.

Various attempts have been made to provide a warm feeling during shaving. For example, shaving foams have been formulated to react exothermically upon release from the shaving canister, so that the foam imparts warmth to the skin, e.g., as described in U.S. Pat. Nos. 3,341,418, 3,772,203, 3,819,524, 3,866,800, and U.S. Pat. No. 3,878,118. However, up to now no self-heating shaving gels have been commercialized even though shaving gels are highly preferred over shaving foams. Thus, it would be highly desirable to provide a post-foaming shave gel product that is self-heating.

SUMMARY

The invention features self-heating post-foaming (or self-foaming) shave gels. The shave gels are heated after dispensing by an exothermic reaction that occurs when two components of the shave gel that are separated prior to delivery are mixed during or after dispensing.

Preferred post-foaming shave gels have a shave gel base that includes a non-ionic surfactant emulsifier, rather than a soap. By "non-ionic" is meant that there is no more than 5%, preferably less than 3%, by weight of any ionic surfactant in the formulation. More preferably, there is no more than 1.5% by weight of any ionic surfactant in the gel compositions. Thus, the preferred shave gels are substantially free of soaps and of anionic surfactants. The non-ionic, soap-free formulation is compatible with and stable in the presence of the actives that are used to generate the warm sensation. The non-ionic shave gel base may also offer additional advantages such as alleviating the problems associated with soap-based products. The shave gel base preferably includes an emulsifier system that includes a blend of fatty alcohol ethoxylates. The blend may include fatty alcohol ethoxylates having relatively longer and shorter polyethylene oxide chains, as will be discussed below. To further increase emulsion stability, amphoteric surfactants may be used as co-surfactants at low levels (e.g. 1%).

In one aspect, the invention features a post-foaming shave gel product comprising an oxidant component and a reductant component. The oxidant component comprises a first shave gel base and an oxidizing agent and the reductant component comprises a second shave gel base and a reducing agent.

In another aspect, the invention features a post-foaming shave gel product including (a) a container having a first chamber and second chamber and at least one dispensing valve for dispensing the contents of said chambers; (b) an oxidant component in the first chamber comprising a first shave gel base and about 2% to about 10% of an oxidizing agent; and (c) a reductant component in the second chamber comprising a second shave gel base and about 2% to about 10% of a reducing agent. The first shave gel base and the second shave gel base each independently include an oil-in-water emulsion including, by weight, about 55% to about 90% water, about 3% to about 20% of a water-dispersible surface active agent capable of forming a lather, and about 1% to about 6% of a volatile self-foaming agent. The oxidizing agent and the reducing agent are selected and are present in such proportion to provide an exothermic reaction upon mixing of the oxidant component and the reductant component during use of the shaving composition.

At least one of the first shave gel base and the second shave gel base may include a non-ionic emulsifier, e.g., a fatty alcohol ethoxylate, preferably a blend of fatty alcohol ethoxylates having different polyoxyethylene chain lengths. The non-ionic emulsifier may include a blend of two surfactants, one of the surfactants being more hydrophobic than the other.

The first shave gel base and the second shave gel base advantageously will be substantially free of soaps and ionic surfactants. By substantially free is meant that the first and second shave gel bases contain less than 3% of soaps and ionic surfactants, preferably less than 1.5% of soaps and ionic surfactants. At least one of the first shave gel base and the second shave gel base may include an emollient and a thickener. The first shave gel base and the second shave gel base preferably will be substantially identical, by which is meant that each shave gel base will have at least three, preferably at least four, more preferably at least five, ingredients identical to those in the other shave gel base and, most preferably, such ingredients will be present in approximately the same proportions as in the other shave gel base.

The oxidizing agent may include a peroxide. The reducing agent may be selected from the group consisting of thiosulfate and sulfite compounds, compounds with a thiourea backbone, and mixtures thereof. One or both of the shave gel bases may include a catalyst selected to catalyze the exothermic reaction between the oxidizing agent and the reducing agent, and/or a neutralizing agent selected to neutralize acid generated by the exothermic reaction between the oxidizing agent and the reducing agent.

One or both of the shave gel bases may further include one or more additives selected from the group consisting of beard wetting agents, skin conditioning agents, foam boosters, emollients, humectants, fragrances, colorants, antioxidants, and preservatives.

Some implementations exhibit one or more of the following advantages. The shave gels provide a pleasant, warm feeling to the user before and during shaving, in combination with the aesthetic properties of a post-foaming gel. The heating effect of the gels helps to hydrate a user's beard and prepare the beard for shaving, improving user comfort. The gels are shelf stable, and dispense from their packaging in an attractive, aesthetic gelled form. After dispensing, the gels provide a smooth, creamy, stable lather that develops quickly when the gels are spread over the skin. The lather remains creamy and stable when the gel is heated. The gels provide desirable performance properties such as lubricity and skin-friendliness, which are maintained during and after heating. The chemistry of the heating system that is used to heat the gel is safe for use on the skin and does not irritate the skin.

Other features and advantages of the invention will be apparent from the description and from the claims.

DETAILED DESCRIPTION

A preferred shave gel base for use in the present invention will include water, a water-dispersible surface active agent (which preferably comprises a non-ionic surfactant), and a volatile self-foaming agent. Preferably the non-ionic surfactant comprises a blend of a relatively hydrophobic non-ionic surfactant and a relatively hydrophilic non-ionic surfactant. A more preferred shave gel base will include, in addition to the aforementioned ingredients, one or more, preferably all, of the following optional ingredients: a water-soluble polymer, a fatty alcohol, an amphoteric surfactant, an emollient (e.g., an oil), and a thickener. The shave gel base is typically in the form of an oil-in-water emulsion.

The shave gel composition is divided into two separate components, (a) an oxidant component containing a first shave gel base and the oxidizing agent and (b) a reductant component containing a second shave gel base and the reducing agent. Any ingredients that could be easily oxidized by the oxidizing agent during the product shelf life are included in the reductant component. These two components are maintained separate in the packaging of the shaving gel composition, as will be discussed further below, and are mixed during or after dispensing. When the two phases are mixed, an exothermic reaction occurs that heats the gel. If the exothermic reaction generates an acid that might tend to irritate the user's skin, one component, preferably the reductant component generally includes a neutralizing agent to neutralize this acid.

The water-dispersible surface active agent, which is preferably a blend of surfactants, is selected to provide several functions. It functions as an emulsifier, solubilizer, detergent, and spreading or dispersing agent. First, the surfactants provide an emulsion that is stable during the shelf life of the product, allowing the product to be dispensed as a gel exhibiting little or no phase separation. Second, the surfactants provide lathering during post-foaming. Third, the surfactants are capable of providing a lather that will remain stable at elevated temperatures, i.e., the temperatures the gel will reach during heating, typically about 35 to 50° C. By "stable," we mean that the lathered gel will not puddle in the user's hand or drip from the user's face, but will instead maintain substantially the same consistency before, during and after heating. The blend of surfactants is generally present in both the oxidant and reductant components, so that both components can be provided as stable emulsions that can be dispensed in gel form.

Preferably, the water-dispersible surface active agent comprises a non-ionic surfactant, more preferably a blend of two or more non-ionic surfactants. Suitable nonionic surfactants have hydrophilic groups, e.g., hydroxyl groups and ether linkages derived from polyhydric alcohols and polyoxyethylene chains. Typically, the lipophilic part of the surfactant may include long hydrocarbon chains, as in the fatty acids, a cyclic hydrocarbon, or a combination of the two. Because they are stable in the presence of mild acids and alkalis, nonionic surfactants provide flexibility of formulation that is generally not possible using soaps.

Suitable surfactant blends may include two or more fatty alcohol ethoxylates, each having a polyethylene oxide chain length of at least 2. Preferred fatty alcohol ethoxylates generally have a fatty alcohol chain length of $C_{12}$ to $C_{24}$, a degree of unsaturation of 0-2, and a polyethylene oxide chain length of 2 to 150 ethylene oxide units. Thus, preferred fatty alcohol ethoxylates have the general formula:

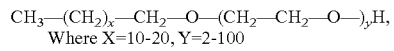
Where X=10-20, Y=2-100

It is generally preferred that the blend of fatty alcohol ethoxylates includes at least one fatty alcohol ethoxylate having a long polyethylene oxide chain length and at least one fatty alcohol ethoxylate having a short polyethylene oxide chain length. Suitable long chain length fatty alcohol ethoxylates have a polyethylene oxide chain length greater than 20, preferably 21 to 150, more preferably 21 to 100. Preferred long chain fatty alcohol ethoxylates include Steareth-100 (100 indicates the polyethylene oxide chain length) and Steareth 21. Other long chain fatty alcohol ethoxylates may be used, e.g., Ceteth-100, Oleth-100 Myreth-100, and Beheneth-100. These surfactants have a preferred HLB range from 15 to 8. Suitable short chain length fatty alcohol ethoxylates have a polyethylene oxide chain length of less than or equal to 20, preferably 2 to 20. Suitable shorter chain length fatty alcohol ethoxylates include, for example, Steareth-2, Steareth-10, Ceteth-20, Steareth-20, Myreth-20, Oleth-20 and Beheneth-20. These surfactants have a preferred HLB range from 4 to 16.

The short and long chain length surfactants are included in a ratio that provides the desired aesthetic and performance properties to the gel. Surfactant levels and types may be selected based on HLB matching of the ingredients (minus surfactants) with the HLB of the surfactant system. It is preferred to use a blend of high and low HLB surfactants to accomplish this. For example Steareth-2 (HLB 4.9) and Stereath-100 (HLB value 18.8) can be blended to give an HLB value of 15. The surfactant level and fatty alcohol level may be further optimized to provide desired stability and formulation aesthetics. Thus, the relative amounts of the two surfactants may be adjusted to obtain a desired balance of properties. For a gel having good consistency and lathering, a suitable ratio of the short polyoxyethylene chain (more hydrophobic) surfactant to the long polyoxyethylene chain (more hydrophilic) surfactant would generally be in the range of 1:1 to 1:3, respectively.

The total amount of the water-dispersible surface active agent in each shave gel base (or in the composition as a whole) is generally in the range of about 3% to about 20%, preferably about 5% to about 15% by weight. Including too high a level of the surfactants may result in a gel that is too stiff and thus does not transition quickly to a foam when spread on the skin, while including too low a level of the surfactants may result in a gel that is not sufficiently stiff and thus may phase separate in the container, or may come out of the container as a foam. The blends of short and long chain fatty alcohol ethoxylates discussed above serve to stabilize the oil droplets, which are distributed in the water phase and in which the blowing gas (self-foaming agent) resides.

It is preferred that one or both shave gel bases include an emollient, to provide desirable cosmetic properties. The oil phase of the emulsion may include any desired emollient that is safe for use in a shaving gel, is compatible with the other ingredients of the composition, and provides the desired aesthetics and in-shave lubricity. Suitable emollients include mineral oil, petrolatum, squalane/squalene, hydrogenated/unsaturated polyisobutene and mixtures thereof. These emollients are suitable for use with the surfactant blends discussed above. Preferably, the composition contains from about 0.25% to 15% of the emollient, more preferably about 0.5% to 12% and most preferably about 0.75% to 8%, by weight of the composition. The emollient is preferably included in both shave gel bases. Non-volatile paraffinic emollients, such as mineral oil, generally also aid in gelling the composition. The term "non-volatile" means that these materials are liquid at room temperature and have a relatively high boiling point (>100° C.).

A thickener is optionally included to improve the consistency and stability of the gel, as well as to adjust its viscosity. The thickener also generally provides body to the foam. A preferred thickener is a fatty alcohol. Suitable fatty alcohols have a chain length of 12-22, and a degree of unsaturation of 0-1. Suitable fatty alcohols include, e.g., myristyl alcohol, lauryl alcohol, cocoyl alcohol, cetyl alcohol, cetearyl alcohol, oleyl alcohol, stearyl alcohol and behenyl alcohol. Generally the composition includes about 1% to 15% by weight of a fatty alcohol thickener.

In addition to, or in some cases instead of the fatty alcohol thickener, the composition may include other thickeners.

Other suitable thickeners include water soluble thickeners, such as hydroxyalkyl cellulose polymers, e.g., hydroxyethyl cellulose and hydroxypropyl cellulose (sold under the trademarks "Natrosol" and "Klucel" respectively), carboxymethyl cellulose, cellulose methyl ether (sold under the trademark "Methocel"), hydroxypropyl starch phosphate (sold under the trademark "Structure XL"), other polysaccharides such as xanthan gum, guar gum, modified starch and carageenan, and mixtures thereof.

Suitable thickeners also include water insoluble thickeners, such as ethoxylated or non-ethoxylated fatty esters, e.g., PEG-150 distearate, PEG-150 pentaerythrityl tetrastearate, pentaerythrityl tetraisostearate, pentaerythrityl tetrastearate, and mixtures thereof.

As a thickener and/or for increased lubricity, the shaving composition may also include a lubricious water soluble polymer. Such polymers will typically have a molecular weight between about 300,000 and 15,000,000 daltons. Suitable polymers include, for example, polyvinylpyrrolidone (PVP), PVP/vinyl acetate copolymer, polyethylene oxide, polyacrylamide, and mixtures thereof.

To formulate a solid gel with good visco-elastic properties, it is generally preferable to include both a water soluble thickener (e.g., polysaccharide polymers, polyethylene oxides) and a water insoluble thickener (e.g., fatty alcohols, pentaerythrityl fatty esters).

The thickener is typically included in an amount sufficient to provide a desired consistency and stability. Generally, the composition includes the thickener at a level of about 0.01% to 15%, preferably about 0.1% to 11%, by weight of the composition. If a lubricious water soluble polymer is included, it is typically provided in an amount of about 0.005% to about 4%, preferably about 0.01% to about 1.5%, by weight. Thickeners are preferably included in both shave gel bases of the composition. It is preferred that the thickener used in the oxidant component is stable in the presence of an oxidizing agent. A suitable thickener for this purpose is polyvinylpyrrolidone (PVP).

As discussed above, the heating reagents generally include an oxidizing agent and a reducing agent. Suitable oxidizing agents include peroxides, e.g., hydrogen peroxide, benzoylperoxide, peroxomonosulfate, peroxodisulfate, urea hydrogen peroxide, and t-butyl peroxide.

Suitable reducing agents are those that will react with the oxidizing agent when the two components of the formulation are mixed, to generate an exothermic reaction. Suitable reducing agents should also be safe for use on human skin in the amounts used in the formulation. The reducing agent may include, for example, thiosulfate and sulfite compounds, such as sodium sulfite, sodium thiosulfate, ammonium thiosulfate, potassium thiosulfate, and thiourea. Other suitable reducing agents include compounds with a thiourea backbone, such as 1,5 diethyl-2-thiobarbituric acid or its derivatives, or ascorbic acid. Mixtures of the above reducing agents, and other suitable reducing agents, may also be used.

Water is the major component of the composition and is used in sufficient quantities to solubilize or disperse the surfactant components and form the continuous phase of the emulsion, while providing a stable gel of suitable viscosity with desirable lathering and rinsing properties. It is added in a sufficient quantity (q.s) to bring the total of all components to 100%. The quantity of water in the composition typically falls within the range of about 55% to 90%, preferably about 60% to 85%.

The oxidizing agent and reducing agent are generally included in stoichiometric proportions, based on the redox reaction that will occur. The redox reaction of hydrogen peroxide with sodium thiosulfate is as follows:

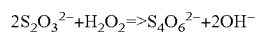
$$2S_2O_3^{2-} + H_2O_2 => S_4O_6^{2-} + 2OH^-$$

In the presence of catalyst the reaction is as follows:

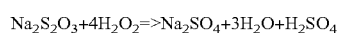
$$Na_2S_2O_3 + 4H_2O_2 => Na_2SO_4 + 3H_2O + H_2SO_4$$

The total amount of the two components is selected to provide a desired level of heat and duration of the exothermic reaction. Preferably, the maximum temperature obtained by the gel during the reaction is from about 30° to 60° C., and this temperature is reached about 10 to 45 seconds after the two components are mixed (this is the temperature the gel reaches when the oxidant and reductant phase of the gel are mixed in a beaker in stoichiometric amounts that provide a total weight of 10 grams of the gel; when a typical amount of 5 to 8 grams of gel are applied to the skin, the actual temperature on the skin is typically about 28° to 45° C.). When the oxidizing agents and reducing agents described above are used, the composition generally includes about 2% to 10% of the oxidizing agent and about 2% to 10% of the reducing agent, in stoichiometric proportions.

To obtain the heat profile described above, it is generally necessary to include a catalyst in the composition. The catalyst is selected to catalyze the exothermic reaction, without deleterious effects on the skin or on the properties of the gel. The catalyst is generally included in the reductant component of the composition. Suitable catalysts for the oxidizing agents and reducing agents described above include sodium molybdate, potassium molybdate, ammonium molybdate, sodium tungstate, potassium tungstate, and mixtures thereof. The composition generally includes from 0 to 1.5% of the catalyst, by weight. The catalyst may be included in one or both of the shave gel bases.

If the exothermic reaction generates an acid, as the reaction of the oxidizing and reducing agents discussed above will generally do, it is preferred that the composition also include a neutralizing agent. The neutralizing agent is selected and is provided in a sufficient amount so as to neutralize enough of the acid so that the composition will not irritate the user's skin. Preferably, substantially all of the acid is neutralized. Suitable neutralizing agents include, for example, triethanolamine, alkaline bicarbonates, oxides and hydroxides, e.g., calcium oxide, potassium bicarbonate, potassium hydroxide and sodium hydroxide. Generally, for the redox chemistries described above, the composition will include about 0.5% to 10% of such a neutralizer. The neutralizeer may be included in one or both of the shave gel bases.

The shaving composition may include additional non-ionic co-surfactants, typically in an amount of about 1% to about 6%, preferably about 2% to about 5%, by weight. The shaving composition may also include additional amphoteric co-surfactants, typically in an amount of 0% to 3.0%, preferably from 0.2% to 1.5%, by weight.

Suitable non-ionic surfactants include the fatty esters of polyhydro alcohols (e.g. polyglyceryl mono oleate), polyoxyethylene fatty esters of glycerides and fatty amides, particularly the alkyl-substituted fatty amides. These surfactants will generally have about 6 to about 100, preferably about 20 to about 50, ethylene oxide units per molecule. Typical non-ionic surfactants include, for example, PEG-40 hydrogenated castor oil and decaglycerol monooleate. Suitable amphoteric surfactants include, for example, the betaines and sultaines such as cocoamidopropyl betaine, coco dimethyl carboxymethyl betaine, coco sultaine and the like. These amphoteric surfactants may tend to function as foam boosters and stabilizers, providing additional heat stability for the foam and preventing puddling. It is preferred that the composition include from about 0.2 to 1.5% of an amphoteric surfactant as a foam booster. Other suitable co-surfactants include sodium lauroyl lactylate, sodium caproyl lactylate, and alkyl polyglucosides.

The post-foaming agent may be any volatile hydrocarbon or halohydrocarbon with a sufficiently low boiling point that it will volatilize and foam the gel upon application to the skin, but not so low that it causes the gel to foam prematurely. The typical boiling point of such an agent generally falls within the range of –20° to 40° C. Preferred post-foaming agents are selected from saturated aliphatic hydrocarbons having 4 to 6 carbon atoms, such as n-pentane, isopentane, neopentane, n-butane, isobutane, and mixtures thereof. Most preferred is a mixture of isopentane and isobutane in a weight ratio (IP:IB) of about 1:1 to about 9:1, preferably about 2:1 to about 7:1, most preferably about 3:1. The post-foaming agent will normally be selected so as to provide a vapor pressure at 20° C. of about 3 to about 20 psig, preferably about 5 to about 15 psig, e.g., about 7 to 8 psig for the preferred 3:1 ratio. The post-foaming agent will be present in an amount to provide the shaving composition with a sufficiently rapid turnover— that is, transition from gel to foam when contacted with the skin—typically, in about 2 to about 30 seconds, preferably in about 5 to about 15 seconds. The post-foaming agent is generally included in both the oxidant and reductant components in an amount of about 1% to about 6%, preferably about 2% to about 5%, by weight, and may be added to concentrates formed by pre-mixing the other ingredients of each component.

Although not necessary to forming a useful shaving composition, other cosmetic ingredients may be advantageously added to improve the application aesthetics and/or achieve other shave benefits. For example, the composition may include one or more of the following components: beard wetting agents, skin conditioning agents (vitamin precursors and derivatives such as e.g., vitamins A, C and E, aloe, allantoin, panthenol, alpha-hydroxy acids, phospholipids, triglycerides, botanical oils, amino acids), foam boosters, emollients (e.g., sunflower oil, fatty esters, squalane), humectants (e.g., glycerin, sorbitol, pentylene glycol), fragrances, colorants, antioxidants, preservatives, and other such ingredients.

The oxidant component and the reductant component are maintained separate from each other until the product is dispensed. This may be accomplished using any desired type of two-component packaging, e.g., as described in U.S. Pat. Nos. 3,241,722, 3,454,198, and 6,250,505, and in co-pending U.S. Ser. No. 10/283,033, filed Oct. 29, 2002, the disclosures of which are incorporated herein by reference. Generally, suitable packaging includes a pressurized container including two chambers, e.g., two bags, and at least one dispensing valve for dispensing the contents of the chambers. The two components are mixed, either automatically during actuation of the dispensing valve or manually by the user after dispensing, to form a uniform gel that becomes warm as the oxidizing and reducing agents react and forms a lather upon spreading on the skin.

As will be illustrated below, the oxidant and reductant components may be formed by adding the oxidizing agent and reducing agent, respectively, to first and second shave gel bases. Preferably, the first and second shave gel bases are substantially identical. Thus, advantageously the oxidizing agent and the reducing agent, respectively, may be added to separate portions of the same shave gel base. The use of a single shave gel base to manufacture both components generally simplifies manufacturing, and may make the two components easier to mix during or after dispensing.

The gels described above may be formed using any suitable manufacturing process. An example of a suitable process is as follows. The thickeners are added to the water and allowed to hydrate over a period of time (30-60 minutes). The entire batch is then heated to 80-90° C. During the heating step, the mineral oil, co-thickeners (fatty alcohol, PEG-150 Distearate) and surfactants are added. The mixture is maintained at 80-90° C. with mixing for 30 minutes. Then the mixture is allowed to cool to room temperature. During the cooling phase, at 75° C., neutralizer is added. The preceding steps form a shave gel base.

To form the reductant phase, actives such as sodium thiosulfate and sodium molybdate are added to the shave gel base formed above, followed by the fragrance and dye, with mixing at 55° C.

To form the oxidant phase, an aqueous solution of hydrogen peroxide is added to the shave gel base and mixed at 35-40° C.

At 35-55° C., each of the oxidant and reductant components are blended with a post-foaming agent at the desired weight percentage range of 3%-4.5%. The shave gel is then packaged in a two-component aerosol gel can, e.g., having a bag-in-bag assembly. It is preferable to place the oxidant component in the inner side of the bag and the reductant component in the outer side of the bag. Even if there is a breach in the bag, having the oxidant phase in the inner bag will generally ensure the integrity of the can.

EXAMPLE

Shave gels were manufactured according to the formulations shown in the following tables. The formulations in the tables are for the oxidant and reductant phases without post-foaming agent. As discussed above, these phases would be mixed with a desired amount and type of post-foaming agent prior to packaging.

Oxidant Phase:

| Ingredients | Example O-1 Wt. % | Example O-2 Wt. % | Example O-3 Wt. % |
|---|---|---|---|
| Water | 66.03 | 64.32 | 65.66 |
| Hydrogen peroxide, 35% soln. | 11.50 | 11.50 | 11.50 |
| Myristyl alcohol | 6.90 | 6.90 | 6.40 |
| Mineral Oil | 6.00 | 6.00 | 6.00 |
| Steareth-100 | 4.72 | 2.80 | 4.72 |
| Ceteth-20 | 4.72 | 8.00 | 4.72 |
| PEG-150 distearate | 0.08 | 0.08 | — |
| Polyvinyl pyrrolidone [Luviskol K-90 Powder] | 0.05 | — | — |
| Poly(vinyl pyrrolidone) [Luviskol K-90], 20% solution | | 0.40 | 0.50 |
| Cetearyl Alcohol (1:1) | — | — | 0.50 |

| Ingredients | Example O-4 Wt. % | Example O-5 Wt. % |
|---|---|---|
| Water | 65.56 | 64.05 |
| Hydrogen peroxide, 35% soln. | 11.50 | 11.50 |
| Myristyl alcohol | 6.00 | 6.40 |
| Mineral Oil | 6.00 | 6.00 |
| Steareth-100 | 4.72 | 4.00 |
| Steareth-20 | 4.72 | 5.50 |
| PEG-150 distearate | 0.10 | 0.05 |
| Polyvinyl pyrrolidone [Luviskol K-90], 20% solution | 0.50 | 0.50 |
| Cetearyl Alcohol (1:1) | 0.90 | 0.50 |

Reductant Phase:

| Ingredient | R-1 Wt. % | R-2 Wt. % | R-3 Wt. % |
|---|---|---|---|
| Water | 64.43 | 67.00 | 67.02 |
| Sodium thiosulfate pentahydrate | 6.50 | 6.50 | 6.50 |
| Myristyl alcohol | 6.00 | 6.00 | 6.00 |
| Mineral oil, 65/75 | 7.50 | 5.00 | 5.00 |
| Steareth-100 | 2.80 | 2.80 | 2.80 |
| Ceteth-20 | 8.00 | 8.00 | 8.00 |
| PEG-150 distearate | 0.15 | 0.08 | 0.08 |
| WSR Sentry Coagulant (PEG-90M) | 0.02 | 0.02 | — |
| Puregel B994(Hydroxypropyl Starch Phosphate) | — | — | 0.50 |
| Vanzan NF-C (Xanthan Gum) | 0.50 | 0.50 | — |
| Natrosol 250 HR(Hydroxyethyl Cellulose) | 0.50 | 0.50 | 0.50 |
| Sodium Molybdate dihydrate | 0.20 | 0.20 | 0.20 |
| Potassium bicarbonate | 1.20 | 1.20 | 1.20 |
| Fragrance, GPC-1599 | 1.50 | 1.50 | 1.50 |
| Ritafactant 122 MS(Cocamidopropyl Betaine and Sodium Caproyl Lactylate) | 0.50 | 0.50 | 0.50 |
| FD & C Blue 1% dye | 0.20 | 0.20 | 0.20 |

| Ingredient | R-4 Wt. % | R-5 Wt. % | R-6 Wt. % |
|---|---|---|---|
| Water | 66.72 | 60.42 | 59.38 |
| Sodium thiosulfate pentahydrate | 6.50 | 6.50 | 6.50 |
| Myristyl alcohol | 6.00 | 6.00 | 7.00 |
| Mineral oil | 5.00 | 5.00 | 6.00 |
| Steareth-100 | 2.80 | 2.80 | 2.80 |
| Ceteth-20 | 8.00 | 8.00 | — |
| Steareth-20 | — | — | 8.00 |
| PEG-150 distearate | 0.08 | 0.08 | 0.20 |
| Puregel B994(Hydroxypropyl Distarch Phosphate) | 0.50 | 0.50 | — |
| Vanzan NF-C (Xanthan Gum) | — | — | — |
| Promidium CO(PPG-2 Hydroxyethyl Cocamide) | — | — | 0.50 |
| Natrosol 250 HR(Hydroxyethyl Cellulose) | 0.50 | 0.50 | — |
| Superfloc N-300 LMW Flocculant(Polyacrylamide) | — | — | 0.02 |
| Sodium Molybdate dihydrate | 0.50 | 1.00 | 0.70 |
| Potassium bicarbonate | 1.20 | — | — |
| Triethanolamine, 99% | — | 7.00 | 7.00 |
| Fragrance, GPC-1599 | 1.50 | 1.50 | 1.50 |
| Ritafactant 122 MS(Cocamidopropyl Betaine and Sodium Caproyl Lactylate) | 0.50 | 0.50 | — |
| FD & C Blue 1% dye | 0.20 | 0.20 | 0.40 |

| Ingredient | R-7 Wt. % | R-8 Wt. % | R-9 Wt. % |
|---|---|---|---|
| Water | 62.70 | 60.10 | 61.70 |
| Sodium thiosulfate pentahydrate | 6.50 | 6.50 | 6.50 |
| Cetyl Alcohol | 5.00 | — | 10.0 |
| Myristyl alcohol | — | 6.50 | — |
| Mineral oil | 0.75 | 5.00 | 0.75 |
| Steareth-21 | 3.90 | — | 3.90 |
| Steareth-2 | 1.10 | — | 1.10 |
| Steareth-100 | — | 4.60 | 13 |
| Steareth-20 | — | 5.70 | — |
| PEG-150 distearate | — | 0.30 | — |
| Cocamidopropyl Betaine (30% active) | 3.00 | — | 4.00 |
| Promidium CO(PPG-2 Hydroxyethyl Cocamide) | — | 0.50 | — |
| Structure XL (Hydroxypropyl Starch Phosphate) | 1.25 | — | 1.25 |
| Polyox WSR N-12K (PEG-23M) | 0.30 | — | 0.30 |
| WSR Sentry Coagulant(PEG-90M) | — | — | — |
| Natrosol 250 HHR(Hydroxyethyl Cellulose) | — | 0.40 | — |
| Natrosol 250 HR(Hydroxyethyl Cellulose) | — | — | — |
| Vanzan NF-C(Xanthan Gum) | — | — | — |
| Superfloc N-300 LMW Flocculant(Polyacrylamide) | — | — | — |
| Cetearyl alcohol | 5.00 | 0.90 | — |
| Polyox WSR 205(PEG-14M) | — | 0.30 | — |
| Sodium Molybdate dihydrate | 1.00 | 0.70 | 1.00 |
| Triethanolamine, 99% | 7.00 | 7.00 | 7.00 |
| Fragrance, GPC-1765 | 2.00 | — | 2.00 |
| Fragrance, GPC-1599 | 1.50 | 1.50 | — |
| FD&C Green #3 (1% dye sol'n) | 0.50 | — | 0.50 |

Any of the reductant phases described above can be used with any of the oxidant phases.

When dispensed and mixed, the formulations described above create a dense warm foam on the skin, comparable to the type of foam that is generally observed when using soap-based post-foaming shaving gels. Application to the skin of an amount of gel suitable for use in shaving (approximately 8 grams) provided a pleasant warming sensation. The foam did not collapse with the heat and lasted for the entire period of shaving.

Other embodiments are within the scope of the following claims.

What is claimed is:

1. A post-foaming shave gel product comprising:
   a container having a first chamber and second chamber and at least one dispensing valve for dispensing the contents of said chambers;
   an oxidant component in the first chamber comprising a first shave gel base and an oxidizing agent;
   a reductant component in the second chamber comprising a second shave gel base and a reducing agent;
   the first shave gel base and the second shave gel base each being an oil-in-water emulsion, and comprising, by weight, about 55% to about 90% water, about 3% to about 20% of a water-dispersible surface active agent capable of forming a lather, and about 1% to about 6% of a volatile self-foaming agent comprising a hydrocarbon or halohydrocarbon having a boiling point in the range of −20C. to 40C.; and
   the oxidizing agent and the reducing agent being selected and being present in such proportion to provide an exothermic reaction upon mixing of the oxidant component and the reductant component during use of the shaving composition;
   wherein the shave gel product comprises no more than 5% of any ionic surfactant; and
   wherein the shaving composition comprises a post-foaming shave gel.

2. The shave gel product of claim 1 wherein the water-dispersible surface active agent of at least one of the first shave gel base and the second shave gel base comprises a non-ionic surfactant.

3. The shave gel product of claim 1 wherein the reducing agent is selected from the group consisting of thiosulfate and sulfite compounds, compounds with a thiourea backbone, and mixtures thereof.

4. The shave gel product of claim 1 wherein the water-dispersible surface active agent of at least one of the first shave gel base and the second shave gel base comprises a blend of two non-ionic surfactants, one of the surfactants being more hydrophobic than the other.

5. The shave gel product of claim 1 wherein at least one of the first shave gel base and the second shave gel base further comprises a catalyst selected to catalyze the exothermic reaction between the oxidizing agent and the reducing agent.

6. The shave gel product of claim 1 wherein at least one of the first shave gel base and the second shave gel base further comprises a neutralizing agent selected to neutralize acid generated by the exothermic reaction between the oxidizing agent and the reducing agent.

7. The shave gel product of claim 1 wherein said water-dispersible surface active agent of at least one of the first shave gel base and the second shave gel base comprises from about 0.2% to about 1.5% of an amphoteric surfactant.

8. The shave gel product of claim 1 wherein said oxidant component and said reductant component are mixed, at least in part, during dispensing.

9. The shave gel product of claim 1, wherein said oxidant component and said reductant component are mixed, at least in part, after dispensing.

10. The shave gel product of claim 1 wherein said oxidant component contains, by weight, about 2% to about 10% of said oxidizing agent.

11. The shave gel product of claim 1 wherein said oxidant component contains, by weight, about 2% to about 10% of said reducing agent.

12. A shave gel product comprising:
    a container having a first chamber and a second chamber and at least one dispensing valve for dispensing the contents of said chambers;
    an oxidant component comprising a first gel base and an oxidizing agent, said oxidizing component located in the first chamber; and
    a reductant component comprising a second gel base and a reducing agent selected from the group consisting of thiosulfate and sulfite compounds, compounds with a thiourea backbone, and mixtures thereof, the second shave composition located in the second chamber;
    wherein the shave gel product comprises a post-foaming shave gel comprising a saturated aliphatic hydrocarbon having 4 to 6 carbon atoms; and
    wherein the shave gel product comprises no more than 5% of any ionic surfactant.

13. The shave gel product of claim 12 wherein the oxidant component and the reductant component are mixed, at least in part, during dispensing.

14. The shave gel product of claim 12 wherein the oxidant component and the reductant component are mixed after dispensing.

15. The shave gel product of claim 1, wherein the hydrocarbon or halohydrocarbon of the volatile self-foaming agent comprises a saturated aliphatic hydrocarbon having 4 to 6 carbon atoms.

16. The shaving gel product of claim 15, wherein the saturated aliphatic hydrocarbon comprises: n-pentane, isopentane, neopentane, isobutene, and mixtures thereof.

17. The shaving gel product of claim 16, wherein the saturated aliphatic hydrocarbon is a mixture of isopentane and isobutene in a weight ratio of about 1:1 to about 9:1.

18. The shaving gel product of claim 1, comprising no more than 1.5% of any ionic surfactant.

19. The shave gel product of claim 1, wherein the shave gel product is substantially free of soaps.

20. The shave gel product of claim 1, wherein the shave gel product is substantially free of anionic surfactants.

* * * * *